(12) United States Patent
Ryba

(10) Patent No.: US 7,104,984 B2
(45) Date of Patent: Sep. 12, 2006

(54) RESHAPEABLE TIP FOR A CRYOPROBE

(75) Inventor: Eric Ryba, Daly City, CA (US)

(73) Assignee: CryoCor, Inc., San Diego, CA (US)

( * ) Notice: Subject to any disclaimer, the term of this patent is extended or adjusted under 35 U.S.C. 154(b) by 0 days.

(21) Appl. No.: 10/646,486

(22) Filed: Aug. 22, 2003

(65) Prior Publication Data

US 2005/0043724 A1   Feb. 24, 2005

(51) Int. Cl.
 *A61B 18/18* (2006.01)
(52) U.S. Cl. .............. 606/20; 606/21; 606/22; 606/23
(58) Field of Classification Search ............ 606/20–26; 128/898
See application file for complete search history.

(56) References Cited

U.S. PATENT DOCUMENTS

| | | |
|---|---|---|
| 4,004,382 A | 1/1977 | Carlson |
| 4,022,215 A | 5/1977 | Benson |
| 4,082,096 A * | 4/1978 | Benson .................. 606/23 |
| 4,207,897 A | 6/1980 | Lloyd et al. |
| 4,211,231 A | 7/1980 | Rzasa |
| 4,456,017 A | 6/1984 | Miles |
| 4,586,923 A | 5/1986 | Gould et al. |
| 4,815,478 A | 3/1989 | Buchbinder et al. |
| 5,114,414 A | 5/1992 | Buchbinder |
| 5,224,943 A | 7/1993 | Goddard |
| 5,345,945 A | 9/1994 | Hodgson et al. |
| 5,354,257 A | 10/1994 | Roubin et al. |
| 5,449,380 A * | 9/1995 | Chin .................... 607/105 |
| 5,800,487 A | 9/1998 | Mikus et al. |
| 5,800,488 A | 9/1998 | Crockett |
| 6,074,412 A | 6/2000 | Mikus et al. |
| 6,106,518 A | 8/2000 | Wittenberger et al. |
| 6,251,105 B1 | 6/2001 | Mikus et al. |
| 6,280,439 B1 | 8/2001 | Martin et al. |
| 6,283,959 B1 * | 9/2001 | Lalonde et al. ............ 606/21 |

(Continued)

OTHER PUBLICATIONS

Meier, B., Carlier, M., Finci, L., Nukata, E., Urban, P., Niederhauser, W., and Favre, J., "Magnum Wire for Balloon recanalization of Chronic Total Coronary Occlusions," *The American Journal of Cardiology*, vol. 64, pp. 148-154, Jul. 15, 1989.

(Continued)

*Primary Examiner*—Rosiland Rollins
(74) *Attorney, Agent, or Firm*—Nydegger & Associates

(57) ABSTRACT

A device for cryoablating exposed tissue having a contoured contact surface includes a tube-shaped shaft and a flexible, thermally conductive enclosure that is attached to the distal end of the tube-shaped shaft. The enclosure is formed with a wall having an outer surface for contacting the target tissue and an inner surface which establishes and surrounds a cryochamber. A shapeable element is attached to the distal end of the shaft and extends into the cryochamber. The element can be permanently deformed into a pre-selected shape to cause a portion of the enclosure wall to conform to the contour of the target tissue. A high-pressure tube in the shaft passes a refrigerant through the shaft for expansion into the cryochamber. This expansion cools the wall of the enclosure, which in turn, extracts heat from the target tissue resulting in the cryoablation of the target tissue.

6 Claims, 1 Drawing Sheet

U.S. PATENT DOCUMENTS

| | | | |
|---|---|---|---|
| 6,471,694 B1 * | 10/2002 | Kudaravalli et al. | 606/21 |
| 6,602,247 B1 * | 8/2003 | Lalonde | 606/22 |
| 6,752,805 B1 | 6/2004 | Maguire et al. | |
| 2002/0169489 A1 | 11/2002 | Dobak, III et al. | |
| 2003/0055416 A1 | 3/2003 | Damasco et al. | |
| 2003/0060814 A1 | 3/2003 | Capuano et al. | |

OTHER PUBLICATIONS

Judkins, M., M.D., "Selective Coronary Arteriography." *Radiology*, vol. 89, No. 5, pp. 815-824, Nov. 1967.

* cited by examiner

RESHAPEABLE TIP FOR A CRYOPROBE

FIELD OF THE INVENTION

The present invention pertains generally to surgical equipment. More particularly, the present invention pertains to surgical cryoprobes for cryoablating exposed tissue. The present invention is particularly, but not exclusively, useful for cryoablating exposed tissue having a contoured surface.

BACKGROUND OF THE INVENTION

Cryosurgical probes have been selectively used in the treatment of a variety of diseases. Functionally, cryosurgical probes have the capability of reducing the temperature of a targeted body tissue to thereby destroy, remove and/or inactivate the tissue. Because of this ability, the use of cryothermal treatment has been prescribed in the treatment of various cancers, including breast cancer and prostate cancer, as well as to remove various tumors, cysts and in the treatment of cataracts. More recently, the use of cryothermal treatment has been shown to be effective in destroying specific conductive tissues of the heart. This technique can be used to block abnormal electrical signals as a treatment for various heart arrhythmias such as atrial fibrillation.

In a typical cryoprobe procedure, the tip of the probe is cooled by a cryo-fluid (e.g. Nitrous Oxide) and the cooled tip is placed in contact with the tissue. This contact causes heat to flow from the tissue and into the probe tip. Because the heat transfer rate is proportional to the contact area between the tissue and probe, it is generally desirable to contact as much of the target tissue as possible. However, in most procedures, the exposed surface of the target tissue is contoured and this contour often precludes the establishment of large or extended contact areas when using a conventional cylindrical probe.

Typically, the exact contour of the target tissue is only known after an internal organ, such as the heart, has been exposed. Once an internal organ such as the heart has been exposed, the procedure must be performed quickly to minimize trauma to the patient. With a standard cylindrical probe tip, multiple contacts are often required to cryoablate even a mildly contoured target tissue. This requirement of multiple contacts is time consuming and can present an increased risk to the patient due to the lengthy duration of the procedure. In addition, the use of multiple contacts can often result in the non-uniform ablation of tissue that can undermine the success of the procedure.

Another case in which a standard cylindrical probe may be inadequate is when the target tissue cannot be adequately exposed for contact with the conventional cylindrical probe. In still other cases, adequate exposure for contact with a conventional cylindrical probe may be possible, but an unreasonable amount of time may be required to effect such an exposure. On the other hand, a probe tip that is reshapeable may be able to access tissue that is otherwise inaccessible or hard to access with a conventional cylindrical probe.

In addition to having an adequate contact area between the probe and tissue, proper heat transfer requires that an unimpeded flow of refrigerant pass through the probe tip. With this in mind, refrigerant flow is an important factor that must be considered when contemplating the reconfiguration of a probe tip to conform with a contoured target tissue.

In light of the above, it is an object of the present invention to provide devices and methods suitable for the purposes of cryoablating exposed tissue in cases where the surface of the exposed tissue is contoured. It is another object of the present invention to provide a tip for a cryoprobe that can be quickly reshaped to conform to the surface of a contoured target tissue, allowing the tip to be reshaped after the target tissue has been exposed. It is yet another object of the present invention to provide a tip for a cryoprobe that can be quickly reshaped with minimal interference to the flow of refrigerant through the tip. Yet another object of the present invention is to provide a reshapeable tip for a cryoprobe and a method for its use that is relatively easy to implement and comparatively cost effective.

SUMMARY OF THE INVENTION

The present invention is directed to a device for cryoablating exposed tissue which may have a contoured contact surface or be somewhat inaccessible using a conventionally shaped cryoprobe. The device includes a tube-shaped shaft that is formed with a lumen and has a proximal end and a distal end. For the present invention, the device further includes a flexible enclosure that is attached to the distal end of the tube-shaped shaft.

In greater structural detail, the flexible enclosure is formed with a wall having an outer surface for contacting the target tissue and an opposed inner surface which establishes and surrounds a cryochamber. In addition to being flexible, the enclosure is made of a material that is thermally conductive to allow heat to pass through the wall of the enclosure and into the cryochamber. For the present invention, the enclosure is formed with an opening that extends through the wall of the enclosure. With this cooperation of structure, the enclosure can be attached to the distal end of the shaft to establish fluid communication through the opening between the lumen of the shaft and the cryochamber.

Also for the present invention, the device includes a shapeable element that is attached to the distal end of the shaft and extends through the opening of the enclosure and into the cryochamber. For the present invention, the shapeable element is sized and made of a suitable material and size to allow the element to be shaped (i.e., plastically deformed) with selected curves, bends and combinations thereof. In a typical embodiment, the shapeable element is made of a relatively soft metal such as annealed or slightly worked copper and is initially shaped as a straight rod. In one embodiment, the shapeable element is designed to be somewhat easily bent or curved by the operating physician using normal hand strength.

The device can further include a high-pressure tube that is positioned in the lumen of the tube-shaped shaft. In one implementation, the high-pressure tube is positioned inside the lumen of the tube-shaped shaft to establish a return line between the inner surface of the tube-shaped shaft and the outer surface of the high-pressure tube. In a typical embodiment, the high-pressure tube extends from the proximal end to the distal end of the tube-shaped shaft.

The device further includes a cryo-fluid supply unit that is positioned to introduce a cryo-fluid such as Nitrous Oxide into the proximal end of the high-pressure tube. The cryo-fluid then traverses through the lumen of the high-pressure tube and exits the high-pressure tube into the cryochamber. In one embodiment, a flow restricting device, such as a capillary tube, can be used to restrict flow at the distal end of the high-pressure tube. In this embodiment, the cryo-fluid passes through the restriction and then expands into the cryochamber to cool the wall of the enclosure. In a particular embodiment of the present invention, the device is designed to ensure that the cryo-fluid transitions from a liquid state to a gaseous state as it expands into the cryochamber. Heat absorbed by the cryo-fluid during this phase transition (i.e., latent heat) cools the wall of the enclosure. After expansion in the cryochamber, the gaseous cryo-fluid passes through the return line and exits the device at the proximal end of the tube-shaped shaft.

In operation, the target tissue is first exposed and the contour of a suitable contact surface on the target tissue is identified. Next, the shapeable element of the device is configured (i.e., shaped) to conform with the identified contour. Because the enclosure is flexible, it follows the shape of the deformed shapeable member. Once shaped, the enclosure is placed in contact with the target tissue and the cryo-fluid supply unit is activated to deliver the cryo-fluid to the cryochamber. The cryo-fluid expands, and in some cases evaporates in the cryochamber and exits through the return line. This expansion and evaporation cools the wall of the enclosure, which in turn, extracts heat from the target tissue resulting in the cryoablation of the target tissue.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
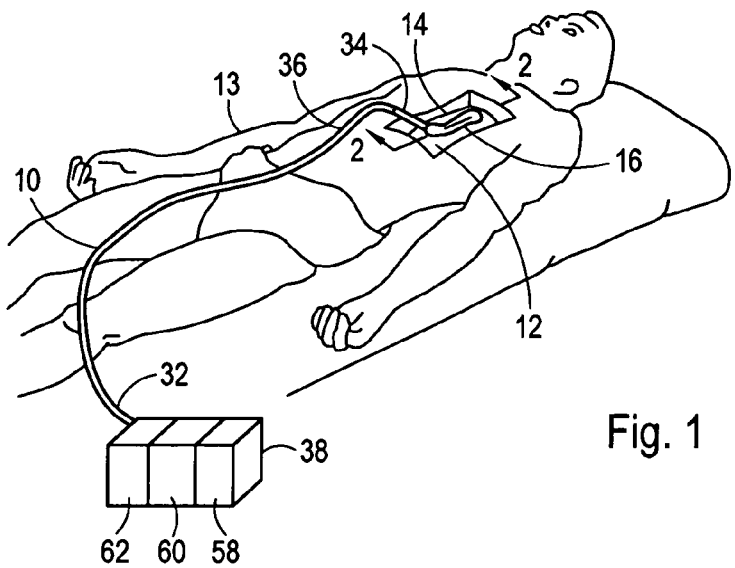
FIG. 1 is a simplified, perspective of a device for cryoablating exposed tissue having a contoured contact surface showing the device operationally positioned to cryoablate internal tissue.

Referring initially to FIG. 1, a device 10 for cryoablating exposed tissue 12 of a patient 13 is shown. In functional overview, the device 10 is particularly suitable for cryoablating exposed tissue 12 having a contoured surface 14 without requiring multiple contacts between the device 10 and the exposed tissue 12. To achieve this functionality, the distal tip 16 of the device 10 is reshapeable to conform with the contoured surface 14.

Figure 2:
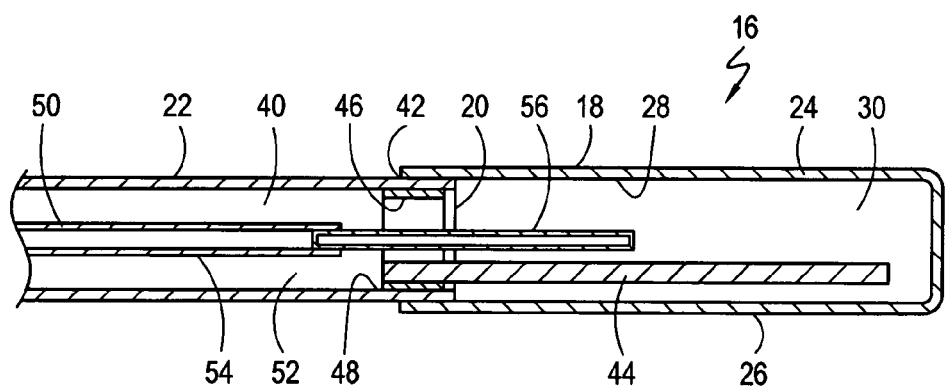
FIG. 2 is a cross-sectional view of the distal end of the device shown in FIG. 1 as seen along line 2—2 in FIG. 1 with the shapeable element and the flexible enclosure shown prior to shaping.

As best seen in FIG. 2, the distal tip 16 includes a flexible enclosure 18 that is attached to the distal end 20 of a tube-shaped shaft 22. As further shown in FIG. 2, the flexible enclosure 18 is formed with a cylindrical shaped wall 24 having an outer surface 26 for contacting target tissue and an inner surface 28, opposed to outer surface 26, which establishes and surrounds a cryochamber 30. For the device 10, the wall 24 of the enclosure 18 is typically made of a flexible, thermally conductive material that will allow heat to pass through the wall 24 and into the cryochamber 30. Preferably, such material will be a composite plastic that is selected for having relatively high thermal conductivities that are in a range from about 2 W/mK up to approximately 100 W/m K.

A better appreciation of the shaft 22 can be obtained with cross-reference to FIGS. 1 and 2. As seen there, the shaft 22 extends from a distal end 20 to a proximal end 32 and can include a distal portion 34 that is typically made of a rigid or semi-rigid material to function as a handle for the physician to position the distal tip 16 of the device 10. As further shown, the shaft 22 can include a proximal portion 36 that is relatively flexible to provide a flexible link between the distal tip 16 of the device 10 and a cryo-fluid supply unit 38 that is described in greater detail below. For the device 10 shown, the shaft 22 is tube-shaped and is formed with a lumen 40 that extends from the proximal end 32 to the distal end 20 of the shaft 22. FIG. 2 further shows the enclosure 18 is formed with an opening 42 and it can be seen that the enclosure 18 is attached to the distal end 20 of the shaft 22 to establish fluid communication through the opening 42 between the lumen 40 of the shaft 22 and the cryochamber 30.

Continuing with FIG. 2, it can be seen that the device 10 includes a shapeable element 44 that is attached to the distal end 20 of the shaft 22 and extends into the cryochamber 30. More specifically, as shown, the shapeable element 44 can be attached (e.g. bonded) to a ring shaped, reinforcing coupling 46, which in turn is attached (e.g. bonded) to the inner surface 48 of shaft 22 at the distal end 20 of the shaft 22. For use in the device 10, the shapeable element 44 is made of a suitable material and size (e.g. thickness) to allow the shapeable element 44 to be shaped (i.e. plastically deformed) with selected curves, bends or combinations thereof. In a typical embodiment, the shapeable element 44 is made of a relatively soft metal such as annealed or slightly worked copper and is initially shaped as a straight rod. Also, the shapeable element 44 is typically designed to be somewhat easily bent or curved by the operating physician using normal hand strength.

Continuing now with cross-reference to FIGS. 1 and 2, it can be seen that the device 10 further includes a high-pressure tube 50 that is positioned inside the lumen 40 of the tube-shaped shaft 22 and extends from the proximal end 32 to a position at or near the distal end 20 of the shaft 22. For the device 10 shown, the high-pressure tube 50 is positioned inside the lumen 40 of the tube-shaped shaft 22 to establish a return line 52 between the inner surface 48 of the shaft 22 and the outer surface 54 of the high-pressure tube 50. FIG. 2 further shows that the device 10 includes a capillary tube 56 that extends from the high-pressure tube 50 and into the cryochamber 30 to restrict the flow of cryo-fluid passing into the cryochamber 30 from the high-pressure tube 50.

As indicated above, the device 10 includes a cryo-fluid supply unit 38 that is positioned to introduce a cryo-fluid such as Nitrous Oxide into the high-pressure tube 50 at the proximal end 32 of the shaft 22. The cryo-fluid then traverses through the high-pressure tube 50, passes through the capillary tube 56 and expands into the cryochamber 30. In one embodiment, the device 10 is designed to ensure that the cryo-fluid transitions from a liquid state to a gaseous state as it expands into the cryochamber 30. Heat absorbed by the cryo-fluid during this phase transition (i.e. latent heat) cools the wall 24 of the enclosure 18. After expansion in the cryochamber 30, the gaseous cryo-fluid passes through the return line 52 and exits the device 10 at the proximal end 32 of the shaft 22.

A suitable cryo-fluid supply unit 38 for delivering a cryo-fluid in a liquid state to the capillary tube 56 for transition to a gaseous state in the cryochamber 30 is disclosed in co-pending U.S. patent application Ser. No. 10/243,997, entitled "A Refrigeration Source for a Cryoablation Catheter" and filed on Sep. 12, 2002, which is assigned to the same assignee as the present invention. Co-pending U.S. application Ser. No. 10/243,997 is incorporated by reference herein. In one implementation, Nitrous Oxide is used as the cryo-fluid with suction applied to the return line 52 allowing the wall 24 of the flexible enclosure 18 to be cooled to a temperature of approximately –85 degrees Celsius.

As disclosed in U.S. application Ser. No. 10/243,997, and shown here schematically in FIG. 1, a typical cryo-fluid supply unit 38 can include a cryo-fluid source 58, such as a gas bottle, which holds the cryo-fluid (e.g. Nitrous Oxide) under pressure (e.g. 750 psia) at ambient temperature (e.g. room temperature). The cryo-fluid supply unit 38 can further include a pressure regulator 60 that is connected in fluid communication with the cryo-fluid source 58 for reducing the pressure on the cryo-fluid down to a working pressure (e.g. approximately 400 psia). During this pressure reduction to the working pressure, the cryo-fluid remains at substantially the ambient temperature.

After pressure on the primary fluid has been reduced to the working pressure, the cryo-fluid supply unit 38 can include a precooler 62 to pre-cool the cryo-fluid from the ambient temperature while substantially maintaining the cryo-fluid at the working pressure. More specifically, at the precooler 62, the cryo-fluid is converted into a fully saturated liquid which has been pre-cooled to a sub-cool temperature. As used here, a sub-cool temperature is one that is below the temperature at which, for a given pressure, the cryo-fluid becomes fully saturated. For example, when Nitrous Oxide is to be used, a sub-cool temperature equal to approximately minus forty degrees Centigrade ($T_{sc}=-40°$ C.) is suitable. The sub-cooled cryo-fluid is then introduced into the high-pressure tube 50 at the proximal end 32 of the shaft 22.

The device 10 can further include one or more measurement sensors (not shown) such as pressure sensors, temperature sensors and combinations thereof, to work in conjunction with a control valve (also not shown) that regulates the flow of cryo-fluid into the high-pressure tube 50 from the precooler 62. In greater detail, the sensors/control valve can be used to maintain a preselected outflow pressure (i.e., the pressure in the return line 52 near the cryochamber 30) to maximize the refrigeration potential of the device 10. More specifically, the refrigeration potential of the device 10 can be maximized by maximizing both the temperature drop the cryo-fluid experiences in the cryochamber 30, and the flow rate of coolant through the cryochamber 30. In one embodiment, Nitrous Oxide is used as the cryo-fluid and the outflow pressure is maintained to be about 15 psia to maximize the refrigeration potential of the device 10. In this embodiment, pressure sensors can be positioned at the distal end 32 of the shaft 22 for use in calculating an outflow pressure. The control valve is then adjusted using the calculated value. Alternatively, one or more sensors can be positioned either in the cryochamber 30 or in the return line 52 to determine an outflow pressure. A more detailed description of a measurement and control system for the device 10 is provided in co-pending U.S. application Ser. No. 10/243,997 which has been previously incorporated by reference.

Figure 3:
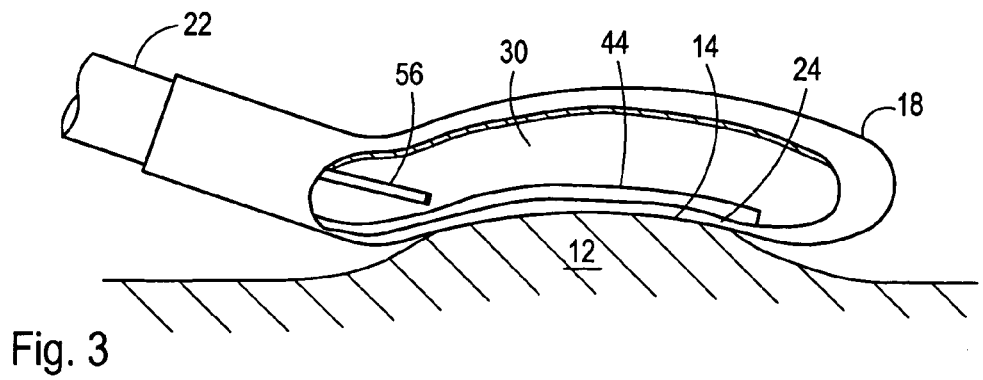
FIG. 3 is an enlarged, perspective view of the distal end of the device shown in FIG. 1 shown operationally positioned against internal tissue having a contoured contact surface and with portions of the flexible enclosure removed for clarity.

The operation of the device 10 can best be appreciated with cross-reference to FIGS. 1 and 3. As shown there, the tissue 12 requiring cryoablation (i.e., target tissue 12) is first exposed and the contour of a suitable contact surface 14 on the target tissue 12 is identified. Next, the shapeable element 44 of the device 10 can be configured (i.e., shaped by bending) to conform with the contour of the surface 14. Because the enclosure 18 is flexible, a portion of the wall 24 of the enclosure 18 follows the shape of the shapeable element 44, as shown in FIG. 3. Once shaped, the enclosure 18 is placed in contact with the target tissue 12 and the cryo-fluid supply unit 38 is activated to deliver a cryo-fluid to the cryochamber 30. The cryo-fluid expands, and in some cases evaporates in the cryochamber 30, and exits through the return line 52 (shown in FIG. 2). This expansion and evaporation cools the wall 24 of the enclosure 18, which in turn, extracts heat from the target tissue 12 resulting in the cryoablation of the target tissue 12.

While the particular reshapeable tip for a cryoprobe as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for cryoablating tissue, said method comprising the steps of:

providing a device including a shaft having a proximal end and a distal end, said device further including a flexible enclosure attached to the distal end of said shaft, said enclosure having an outer surface and an inner surface, with the inner surface thereof forming a cryochamber wherein the cryochamber has a length, said device further including a shapeable rod attached to the distal end of said shaft and extending therefrom into the cryochamber substantially along and through the length thereof;

exposing the tissue;

manually deforming said shapeable rod to selectively establish a configuration for said enclosure to conform said enclosure to the exposed tissue;

contacting the tissue with said outer surface of said enclosure;

preconditioning a cryo-fluid to approximately 400 psia and –40° C.; and passing said preconditioned cryo-fluid through a flow restricting device and into said enclosure to flow to said enclosure unimpeded by said rod to cool said enclosure and cryoablate the tissue.

2. A method as recited in claim 1 wherein the tissue is myocardial tissue.

3. A method as recited in claim 1 wherein said deforming step is performed subsequent to said exposing step.

4. A method as recited in claim 1 wherein the tissue has an exposed surface and wherein said deforming step establishes a configuration for said enclosure wherein a portion of said outer surface of said enclosure substantially conforms with a portion of the exposed surface of the tissue.

5. A method as recited in claim 1 wherein said shapeable rod is made of copper.

6. A method as recited in claim 1 wherein said passing step comprises the steps of:

holding said cryo-fluid in a liquid state;

flowing said cryo-fluid through a high-pressure tube; and thereafter flowing said cryo-fluid through a capillary tube to transition said cryo-fluid from said liquid state into a gaseous state to cool said enclosure.

* * * * *